United States Patent

Balthasart et al.

[11] Patent Number: 5,574,191
[45] Date of Patent: Nov. 12, 1996

[54] PROCESS FOR THE MANUFACTURE OF 1,1,1-TRIHALOETHANES

[75] Inventors: Dominique Balthasart, Brussels; Pascal Pennetreau, Rixensart, both of Belgium

[73] Assignee: Solvay (Société Anonyme), Brussels, Belgium

[21] Appl. No.: 533,453

[22] Filed: Sep. 25, 1995

[30] Foreign Application Priority Data

Sep. 26, 1994 [FR] France .................................. 94 11564

[51] Int. Cl.$^6$ ..................................................... C07C 17/08
[52] U.S. Cl. .......................... 570/166; 570/167; 570/168; 570/169
[58] Field of Search .................................... 570/166, 167, 570/168, 169

[56] References Cited

U.S. PATENT DOCUMENTS

| | | |
|---|---|---|
| 2,669,590 | 2/1954 | Miller et al. . |
| 3,836,479 | 9/1974 | Pansksch et al. . |
| 5,008,474 | 4/1991 | Wairaevens et al. . |
| 5,051,538 | 9/1991 | Gumprecht .................... 570/166 |
| 5,367,102 | 11/1994 | Janssens et al. . |
| 5,382,721 | 1/1995 | Pennetreau et al. . |

FOREIGN PATENT DOCUMENTS

| | | |
|---|---|---|
| 0391102 | 10/1990 | European Pat. Off. . |
| 0574077 | 12/1993 | European Pat. Off. . |
| 2124239 | 9/1972 | France . |
| 2365542 | 4/1978 | France . |
| WO91/18852 | 12/1991 | WIPO . |

OTHER PUBLICATIONS

G. A. Olah et al; Journal of Organic Chemistry, "Organic Fluorine Compounds. XXXIII Electrophilic Additions to Fluoro Olefins in Superacids", 1972, vol. 37, No. 7.

*Primary Examiner*—Alan Siegel
*Attorney, Agent, or Firm*—Spencer & Frank

[57] ABSTRACT

1,1,1-Trifluoroethane is produced, in addition to 1,1,-dichloro-1-fluoroethane and/or 1-chloro-1,1-difluoroethane, by hydrofluorination in the liquid phase, using hydrogen fluoride, vinylidene fluoride and at least one chloro compound chosen from vinylidene chloride and 1,1,1-trichloroethane.

11 Claims, 1 Drawing Sheet

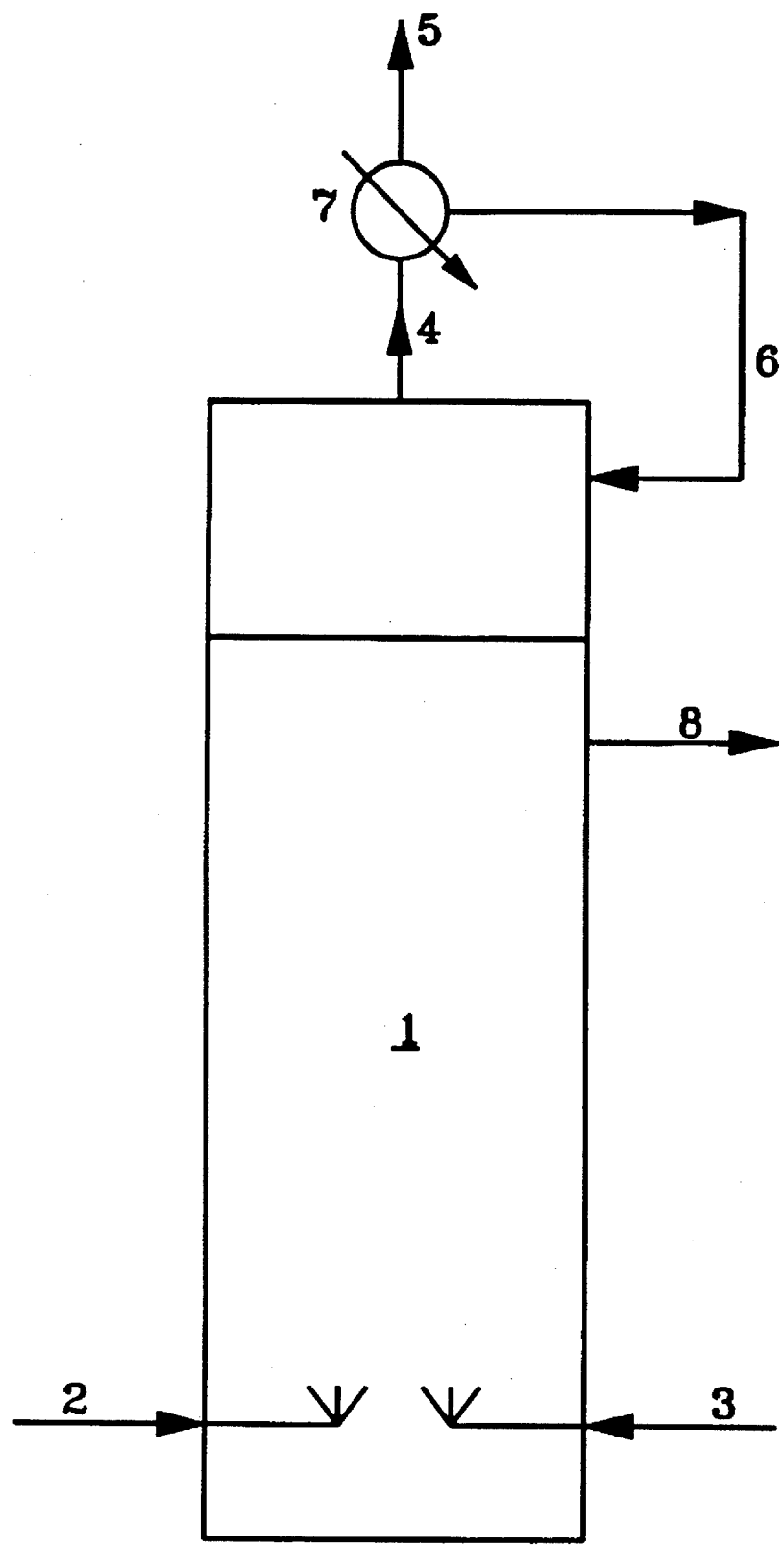

PROCESS FOR THE MANUFACTURE OF 1,1,1-TRIHALOETHANES

FIELD OF THE INVENTION

The present invention relates to a process for the manufacture of 1,1,1-trihaloethanes, in particular to a process for the manufacture of 1,1,1-trifluoroethane, in addition to 1,1-dichloro-1-fluoroethane and/or 1-chloro-1,1-difluoroethane.

TECHNOLOGY REVIEW 1,1,1-Trifluoroethane (referred to hereinbelow as HFC-143a) appears to be usable in particular as a refrigerant, as a replacement for totally halogenated chlorofluorocarbons (CFCs), which are being progressively banned on account of their possible harmful action on stratospheric ozone.

1,1-Dichloro-1-fluoroethane (referred to hereinbelow as HCFC-141b) may also be used as a replacement for certain CFCs, mainly as a swelling agent for polymer foams and as a solvent.

1-Chloro-1,1-difluoroethane (referred to hereinbelow as HCFC-142b) may also be used as a replacement for certain CFCs, mainly as a swelling agent for polymer foams. It is also an intermediate product in the synthesis of vinylidene fluoride.

It is known, in particular from Patent U.S. Pat. No. 2,669,590, to prepare HFC-143a by reaction of vinylidene fluoride (VF2) with hydrogen fluoride in the gas phase, in the presence of a catalyst. The production efficiency of such a process per unit of reactor volume is, however, very poor.

It is moreover known to prepare HFC-143a starting with the same reactants, in the liquid phase, at a temperature of −50° C., in the presence of antimony pentafluoride as catalyst (Olah G. A. and Mo Y. K.; Journal of Organic Chemistry, (1972), Vol. 37, No. 7). The antimony pentafluoride used in this process is, however, gradually converted into antimony trifluoride, which is inactive as a catalyst and is particularly corrosive towards metallic materials.

The known processes for the hydrofluorination in the liquid phase of vinylidene chloride (referred to hereinbelow as VC2) or of 1,1,1-trichloroethane (referred to hereinbelow as T111) do not make it possible to obtain high yields of HFC-143a. Indeed, these known processes essentially produce HCFC-141b and HCFC-142b. In conditions such as those adopted in the process described in International Application WO 91/18852, in which VC2 is hydrofluorinated in the liquid phase in the absence of catalyst and at a temperature of 75° to 130° C., the molar fraction of the HFC-143a formed does not exceed about 4% of all the products formed. Under conditions which favour more extensive fluorination of halogenated 2C reactants, for example at a higher temperature and in the presence of very active hydrofluorination catalysts, such as antimony salts, HCFC-142b is mainly formed, and recycling of this into the reactor does not make it possible to achieve a production efficiency for HFC-143a which is satisfactory from an industrial point of view. In addition, under these conditions, there is a risk of forming a large amount of undesired heavy by-products, mainly oligomers.

SUMMARY OF THE INVENTION

The present invention is consequently directed towards providing a process for the preparation of HFC-143a which no longer has the drawbacks of the processes mentioned above and which may readily be carried out industrially.

The present invention is also directed towards a process for the manufacture of HFC-143a and, in addition, HCFC-141b and/or HCFC-142b, in which the desired products are formed in highly modifiable proportions, depending on their respective needs.

The present invention is also directed towards providing a process which makes it possible to increase the proportion of HFC-143a co-produced with HCFC-141b and/or HCFC-142b in the existing processes for the hydrofluorination of VC2 or of T111 in the liquid phase, without simultaneously giving rise to the formation of large amounts of heavy by-products.

BRIEF DESCRIPTION OF THE DRAWING

The drawing diagrammatically illustrates an advantageous embodiment of the process according to the invention.

DETAILED DESCRIPTION OF THE INVENTION

The invention consequently relates to a process for the manufacture of 1,1,1-trifluoroethane (HFC-143a) and, in addition, 1,1-dichloro-1-fluoroethane (HCFC-141b) and/or 1-chloro-1,1-difluoroethane (HCFC-142b), in which process hydrogen fluoride (HF), vinylidene fluoride (VF2) and at least one chloro compound chosen from vinylidene chloride (VC2) and 1,1,1-trichloroethane (T111) are reacted together, in the liquid phase.

The reaction between HF, VF2 and the chloro compound is generally carried out in the liquid phase in a liquid reaction medium containing HCFC-141b. in this embodiment of the process according to the invention, the HCFC-141b of the reaction medium is advantageously that co-produced with HFC-143a. The weight content of HCFC-141b in the reaction medium is preferably greater than 40%. In a particularly preferred manner, it is more than 50% by weight. Generally, the HCFC-141b content in the reaction medium does not exceed 80%. Besides the reactants (HF, VC2 or T111, and VF2) and the desired reaction products (HFC-143a, HCFC-141b and HCFC-142b), the reaction medium advantageously also contains heavy by-products, mainly VC2 chlorofluoro oligomers. The composition of the reaction medium may be adjusted by controlled evacuation of the reaction products in two forms: evacuation in gas form and evacuation in liquid form.

In the process according to the invention, the reaction of HF, VF2 and the chloro compound may be carried out in the presence or in the absence of a hydrofluorination catalyst. In one specific embodiment of the process, the abovementioned reaction is carried out in the presence of a hydrofluorination catalyst selected from compounds of the elements from groups IIIa, IVa and b, Va and b and VIb of the Periodic Table of the Elements. Compounds of titanium, boron, tin, antimony, tantalum and of molybdenum are more particularly used. The tin or antimony compounds are very suitable for use, those of tin being more particularly preferred when the chloro compound is VC2, and those of antimony when the chloro compound is T111. As compounds which may be used as catalysts, there may be mentioned the salts and more particularly the halides. A choice is preferably made from among the chlorides, the fluorides and the chlorofluorides. Tin tetrachloride has proved to be particularly advantageous. A compound of formula $SnCl_{4-x}F_x$ with x between 0 and 4, is most particularly preferred. Such a compound may be obtained by a treatment, preferably prior to placing $SnCl_4$ in contact with the VF2 and the chloro compound, using hydrogen fluoride. When a catalyst is used in the process according to the invention, the amount of catalyst used may vary within a wide range. Usually, the catalyst is used in an amount of at least 0.001 mol per kg of reaction medium, preferably of at least 0.01 mol/kg. In general, not more than about 2 mol of catalyst are used per kg of reaction medium. Usually, the amount of catalyst does not exceed about 1 mol per kg of reaction medium.

The process according to the invention is generally carried out at a reaction temperature at least equal to 20° C. The reaction temperature is preferably at least 40° C. In a particularly preferred manner, it is at least equal to 60° C. Usually, the reaction temperature does not exceed 150° C. It advantageously does not exceed 130° C. A temperature not exceeding 120° C. is preferred.

The pressure at which the reaction is conducted is not critical per se, as long as it allows the reaction to be carried out in the liquid phase, that is to say that it is sufficient to maintain the reaction medium in essentially liquid form. It varies depending on the temperature at which the reaction medium is maintained. This pressure may be the autogenous pressure, a higher pressure generated by the introduction of an inert gas, such as nitrogen for example, or a lower pressure obtained by dilution of the reaction medium with an inert organic solvent, such as 1,2-dichloroethane for example. Generally, the reaction is carried out at a pressure at least equal to 2 bar, preferably at least equal to 5 bar. The pressure usually does not exceed 30 bar. It advantageously does not exceed 20 bar.

In the process according to the invention, the proportion between the amount of HFC-143a formed and the amount of HCFC-141b and/or of HCFC-142b which are formed may be adjusted at will, by appropriately adjusting the molar ratio of VF2 to the sum of VF2 and chloro compound being used. In general, the molar ratio between the VF2 used and the sum of VF2 and chloro compound used is at least 0.01. It is usually at least equal to 0.05. This molar ratio generally does not exceed 0.75. It advantageously does not exceed 0.5.

In the absence of catalyst, the process according to the invention leads mainly to the formation of HFC-143a and HCFC-141b, the amount of HCFC-142b formed being low. On the other hand, in the presence of a catalyst, HFC-143a and HCFC-142b are formed in the majority, the amount of HCFC-141b formed being less than that obtained in the absence of catalyst.

In the process according to the invention, hydrogen fluoride is advantageously introduced in a molar ratio of HF to the sum of the VF2 and chloro compound at least equal to 1. This molar ratio usually does not exceed 20. The process is preferably performed with a molar ratio of 1.5 to 15.

In the process according to the invention, the HF and the VF2 may be placed in contact prior to placing in contact with the chloro compound. It is possible in particular to inject VF2 into the unreacted HF separated from the reaction products and recycled into the hydrofluorination reactor of the chloro compound. Conversely, the HF and the chloro compound may also be placed in contact prior to placing in contact with the VF2. It is thus possible, for example, to introduce the VF2 at the stage of separation of the products obtained by hydrofluorination of the chloro compound, in particular by injection into a distillation column used to separate the reaction products. Preferably, the HF, the VF2 and the chloro compound are introduced into the same reaction zone in which the HF reacts simultaneously with the VF2 and the chloro compound. Despite the presence of hydrogen chloride (HCl) in the reaction medium, generated by the reaction between HF and the chloro compound, it was observed that VF2 reacts much more with HF to form HFC-143a, rather than with HCl to form HCFC-142b.

Under the conditions described above, the reaction may be performed in a batchwise or continuous manner. It is advantageously carried out continuously.

The reaction may be performed in conventional equipment, which is well known to those skilled in the art. This may consist of several reactors arranged in series or, preferably, of a single reactor, supplied with the starting materials (VC2 or T111, VF2, HF) and the recycled materials, in gas or liquid form and heated or cooled in an appropriate manner. The mode of introduction and the rates of flow of the reactants and the possible recycled materials into the reactor are adjusted so as to maintain suitable proportions in the reaction medium, leading to production of HFC-143a and, in addition, HCFC-141b and/or HCFC-142b in the desired proportions. The reactor is generally fitted with a device for withdrawing gas. A column and a reflux condenser may, for example, be mounted on the reactor. This device makes it possible to avoid entrainment, in the gas stream leaving the reactor, of the catalyst or catalysts optionally used, and to adjust the composition of this gas stream. The reactor is advantageously also fitted with a means for withdrawing liquid. The withdrawal means are generally adjusted so as to allow essentially all of the HCl produced to be withdrawn in the gas phase. When a high proportion of HCFC-142b is desired, the gas-phase-withdrawal device is advantageously adjusted so as to allow this product to be withdrawn in gas form.

The process according to the invention has the appreciable advantage of an HFC-143a production efficiency which is greatly superior to that achieved by the existing processes for the hydrofluorination of VC2 or of T111 in the liquid phase. It allows existing plants for the production of HCFC-141b or HCFC-142b to be converted inexpensively into units for the joint and adjustable production of these products and of HFC-143a. Depending on the operating conditions adopted, the process according to the invention allows the distribution of the desired products, that is to say HFC-143a, HCFC-141b and HCFC-142b, to be varied within a wide range.

The plant represented diagrammatically in the figure comprises a reactor 1, a pathway 2 for the introduction of HF into the reactor 1, a pathway 3 for the introduction of a mixture of VC2 or of T111 and VF2 into the reactor 1, a pathway 8 for withdrawal of liquid from the reactor 1 and a pathway 4 for withdrawal of gas from the reactor. A condenser 7 is mounted over the reactor 1, which condenser is in communication with the pathway 4, with a pathway 6 for recycling a condensate to the reactor 1, and with a pathway 5 for evacuation of a gas.

According to one specific embodiment of the process according to the invention, HF, VF2 and the chloro compound are placed in contact in the reactor 1 in the absence of any catalyst, preferably at a temperature of 70° to 110° C., the temperature of the condenser is adjusted so that the gas withdrawn via the pathway 5 contains HFC-143a, HCFC-142b and HCl, and some of the reaction medium is withdrawn, in the liquid phase, via the pathway 8, from which medium HCFC-141b and HCFC-142b are separated in a conventional manner. At least part of the HCFC-142b co-produced may be recycled into the reactor 1. Under these conditions, HFC-143a and HCFC-141b are mainly produced. This embodiment of the process according to the invention is preferred.

According to a second specific embodiment of the process according to the invention, HF, VF2 and the chloro compound are placed in contact in the reactor 1, preferably at a temperature of 60° to 120° C., in the presence of a hydrofluorination catalyst, this catalyst advantageously being a tin or antimony halide, the temperature of the condenser is adjusted so that the gas withdrawn via the pathway 5 mainly contains HCFC-141b, HCFC-142b, HFC-143a and HCl, from which withdrawn gas HCFC-141b, HCFC-142b and HFC-143a are separated in a conventional manner. Part of the HCFC-141b co-produced may be recycled into the reactor 1. Under these conditions, HFC-143a and HCFC-142b are mainly produced.

EXAMPLES

The examples which follow illustrate the invention in a non-limiting manner.

Example 1

HF, VC2 and VF2 in a 23.5/13.9/1 molar ratio were injected continuously into a reactor as represented diagrammatically in FIG. 1, maintained at a temperature of 88° C. and a pressure of 11 bar, containing a liquid reaction medium consisting mainly of HCFC-141b and containing 1 g of tin chloride per kilo of reaction medium. The gas stream recovered at the condenser outlet maintained at 65° C. was analysed. 99.9% of the VF2 and 99.7% of the VC2 used were converted. The distribution of the desired products, that is to say the ratio between the amount of each of these products formed and the sum of the amounts of HCFC-141b, HCFC-142b and HFC-143a formed, expressed as a molar percentage, was 39.6% of HCFC-141b, 54.3% of HCFC-142b and 6.1% of HFC-143a.

Example 2

(comparison)

The test of Example 1 was repeated without introduction of VF2 into the reactor. The distribution of the desired products was 41.6% of HCFC-141b, 57.2% of HCFC-142b and 1.2% of HFC-143a.

On the basis of the results of Examples 1 and 2, it was calculated that, in the process of Example 1 in accordance with the invention, at least 84% of the VF2 introduced into the reactor was converted into HFC-143a.

What is claimed is:

1. A process for the manufacture of 1,1,1-trifluoroethane and, in addition, 1,1-dichloro-1-fluoroethane and/or 1-chloro-1,1-difluoroethane, by reaction in the liquid phase of hydrogen fluoride, vinylidene fluoride and at least one chloro compound chosen from vinylidene chloride and 1,1,1-trichloroethane, wherein said hydrogen fluoride, vinylidene fluoride and at least one chloro compound are introduced into a reaction zone in which the hydrogen fluoride reacts simultaneously with the vinylidene fluoride and the chloro compound at a temperature of at least 20 C. and which does not exceed 150 C.

2. The process of claim 1, in which the reaction is carried out in a liquid medium containing from 40% to 80% by weight of HCFC-141b.

3. The process of claim 1, in which the reaction is carried out at a temperature of 40° to 130° C.

4. The process of claim 1, in which the reaction is carried out in the absence of catalyst.

5. The process of claim 1, in which the reaction is carried out in the presence of a hydrofluorination catalyst selected from compounds of the elements from groups IIIa, IVa and b, Va and b and VIb of the Periodic Table of the Elements.

6. The process of claim 1, in which the molar ratio of the VF2 to the sum of the VF2 and chloro compound used is from 0.01 to 0.75.

7. The process of claim 1, in which the molar ratio of the hydrogen fluoride to the sum of the VF2 and chloro compound used is from 1 to 20.

8. The process of claim 1, in which the reaction is conducted continuously.

9. The process of claim 1, wherein said reaction in the liquid phase is carried out in a liquid reaction medium containing 1,1-dichloro-1-fluoroethane.

10. The process of claim 1, wherein said chloro compound is vinylidene chloride.

11. A process for the manufacture of 1,1,1-trifluoroethane and at least one compound selected from the group consisting of 1,1-dichloro-1-fluoroethane and 1-chloro-1,1-difluoroethane, said process comprising simultaneously reacting hydrogen fluoride, vinylidene fluoride and at least one chloro compound selected from the group consisting of vinylidene chloride and 1,1,1-trichloroethane in a liquid phase at a temperature from 40° to 130° C. in the absence of a catalyst, and in which the molar ratio of the vinylidene fluoride to the sum of the vinylidene fluoride and chloro compound is from 1 to 20.

* * * * *